US012642451B2

(12) United States Patent
     Koeppe

(10) Patent No.: US 12,642,451 B2
(45) Date of Patent: Jun. 2, 2026

(54) SENSOR NETWORK

(71) Applicant: SENDANCE GMBH, Linz (AT)

(72) Inventor: Robert Koeppe, Linz (AT)

(73) Assignee: SENDANCE GMBH, Linz (AT)

( * ) Notice: Subject to any disclaimer, the term of this patent is extended or adjusted under 35 U.S.C. 154(b) by 397 days.

(21) Appl. No.: 18/573,412

(22) PCT Filed: Jun. 23, 2022

(86) PCT No.: PCT/AT2022/060213
     § 371 (c)(1),
     (2) Date: Dec. 21, 2023

(87) PCT Pub. No.: WO2023/272319
     PCT Pub. Date: Jan. 5, 2023

(65) Prior Publication Data
     US 2024/0298924 A1      Sep. 12, 2024

(30) Foreign Application Priority Data

Jun. 28, 2021    (AT) .................................. A 118/2021

(51) Int. Cl.
     *G01B 7/004*        (2006.01)
     *A61B 5/00*         (2006.01)
     *A61B 5/11*         (2006.01)
(52) U.S. Cl.
     CPC .............. *A61B 5/11* (2013.01); *A61B 5/6804* (2013.01); *G01B 7/004* (2013.01); *A61B 2562/046* (2013.01); *A61B 2562/164* (2013.01)
(58) Field of Classification Search
     CPC ... A61B 5/11; A61B 5/6804; A61B 2562/046; A61B 2562/164; G01B 7/004
     See application file for complete search history.

(56)                References Cited

U.S. PATENT DOCUMENTS 10,386,224  B2 *   8/2019   Shim ....................... G01L 1/205
 2010/0238636  A1 *   9/2010   Mascaro .............. H05K 1/0283
                                                            361/749
                        (Continued)

FOREIGN PATENT DOCUMENTS

CA            2844826  A1 *   2/2013   ........... G01N 27/048
CN         103119542  B  *   8/2016   ........... G06F 1/1692
                        (Continued)

OTHER PUBLICATIONS

International Search Report and Written Opinion in International Application No. PCT/AT2022/060213, mailed Oct. 11, 2022, 15 pages.

*Primary Examiner* — Jamel E Williams
(74) *Attorney, Agent, or Firm* — Liang & Hennessey LLP; Brian Hennessey

(57)                ABSTRACT

A network including sensor points that form the node points of the network and elongated connecting elements that form the edges of the network, wherein the connecting elements each have an extensible substrate on which there is at least one conductor that runs from one end region of the connecting element in the longitudinal direction thereof to a second end region of the connecting element. The conductor consists of a non-extensible material and the conductor has a sinuous or zigzag progression on the extensible substrate, such that the individual sections of the conductor run transverse to the longitudinal direction of the respective connecting element.

22 Claims, 9 Drawing Sheets

(56)          References Cited

U.S. PATENT DOCUMENTS

| 2017/0303853 | A1 * | 10/2017 | McMillen | ............ | A61B 5/6843 |
| 2018/0249767 | A1 * | 9/2018 | Begriche | ................ | A41D 1/005 |
| 2020/0060558 | A1 * | 2/2020 | Aleksov | .............. | A61B 5/7278 |

FOREIGN PATENT DOCUMENTS

| CN | 106489123 | A | * | 3/2017 | ............. | G06F 3/047 |
| CN | 206818346 | U | * | 12/2017 | | |
| CN | 104541236 | B | * | 6/2018 | .......... | G06F 3/0443 |
| CN | 109341727 | A | * | 2/2019 | .............. | G01D 5/12 |
| EP | 3621088 | A1 | * | 3/2020 | .......... | H05K 1/0283 |
| WO | WO-2017013493 | A1 | * | 1/2017 | .......... | A61B 5/0205 |

* cited by examiner

<u>Fig. 1</u>

SENSOR NETWORK

CROSS-REFERENCE TO RELATED APPLICATIONS

The present application is a national phase application of PCT Application No. PCT/AT2022/060213, filed Jun. 23, 2022, entitled "SENSOR NETWORK", which claims the benefit of Austrian Patent Application No. A 118/2021, filed Jun. 28, 2021, each of which is incorporated by reference in its entirety.

BACKGROUND OF THE INVENTION

1. Field of the Invention

The invention relates to a flexible sensor network.

2. Description of the Related Art

A sensor network comprises several individual sensors, which are present at nodes of the network and are interconnected by the network structure.

Such sensor networks can be realized with conventional sheathed conductors such as stranded cables, which serve as connections between the sensors of the network. The sensors can be flexibly arranged on a surface in that their distance can be smaller than or equal to the length of the stranded cables. The disadvantage is that if the distance between the sensors is smaller than the length of the stranded cable, it either protrudes from the surface or has to be laid out in a winding path.

This prior art is known, for example, from CN109341727A, in which the connecting elements are designed as insulated conductors and have a winding path throughout.

In EP3621088A1, US2017303853A1, US2018249767A1 and WO2017013493A1, flexible connections are used to realize predefined circuits.

In US2010238636A1 and US2020060558A1, circuits are molded entirely in flexible material.

The task underlying the invention is to create a flexible sensor network that is simple to manufacture and allows flexible attachment of the individual sensors to a surface.

For solving the task, a sensor network proposed, as well as its use on a body and methods for performing measurements with the sensor network.

In particular, a two-dimensional network is proposed comprising sensor points forming the nodes of the network and elongated connecting elements comprising a substrate and a conductor, which connecting elements form the edges of the network, the network having in each of its two dimensions at least two edges forming grid lines of the network, the network of sensor points and connecting elements being open in the region between the edges, wherein at each sensor point a current flow or capacitive coupling can take place from the conductors of a first grid line to the conductors of a second grid line, wherein the first and second grid lines are transverse to each other and the current flow or capacitive coupling is dependent on a measurand of the sensor point, wherein the connecting elements each comprise a stretchable substrate, which substrate is present as a straight strip on which at least one conductor is present, which extends from one end region of the connecting element along the longitudinal direction thereof to a second end region of the connecting element, wherein the conductor consists of a non-stretchable material and the conductor has a wound or bent course on the stretchable substrate, so that the individual sections of the conductor extend transversely to the longitudinal direction of the respective connecting element.

In one embodiment, the sensor network comprises a plurality of sensor points and a plurality of stretchable connection elements each comprising at least one conductor, wherein the sensor points are connected to the stretchable connection elements to form a two-dimensional grid structure.

Preferably, the sensor network is produced by first producing sensor points and connecting elements, in particular separately from each other, and then connecting the sensor points by attaching the connecting elements to form a sensor network. Afterwards, the finished sensor network can be attached to a body.

In particular, a physical body or physical object is to be understood as "body".

The network can be applied to a surface of a freely shaped component curved in two dimensions without having to specially adjust the connecting lengths in advance. Due to the mesh structure, the connecting elements only have to be stretchable in one dimension. Different surfaces can be created using a uniform manufacturing method (linking of sensor points). Thus, a standard sensor network can be integrated into a custom-made component. Examples include orthoses, prosthetic sockets, ski boots, insoles or seat shells specially adapted to the wearer.

The sensor points preferably have a regular shape. Preferably, the sensor points can have a round or square, or octagonal outer perimeter, or be square with rounded or chamfered corners. Preferably, each sensor point has four outer edges, wherein opposing outer edges are preferably aligned parallel to each other. Preferably, the four outer edges are designed identically to each other. The sensor points can have a unique marking, in particular in a corner area, or a unique shape, for example by chamfering one corner, so that the alignment of the sensor points in the grid arrangement is apparent, in particular to prevent incorrect assembly.

Preferably, the sensor points have a diameter or a distance between two opposite edges in the range of 3 mm to 3 cm, especially preferably 5 mm to 2 cm. Preferably, the sensor points are small-area, thin films with electrically active layers. Preferably, the sensor points measurably change at least one of their electrical properties upon an external impact.

The sensor points are spaced apart to each other, preferably in several parallel rows.

The sensor points are connected to the respective directly adjacent sensor points of the network by stretchable connecting elements, which are preferably stretchable to at least 125%, in particular at least 150%, especially preferably 200% of their unstretched length, without changing the resistance of the electrical conductor of the connecting element. The stretchability of the connecting element is preferably in the range of 1.25 to 3 times of its unstretched length. The substrate of the connecting elements is elastically deformable in this range. The substrate can thus be elastically deformed to at least 1.25 times, preferably at least 1.5 times, in particular at least twice of its unstretched length.

The distance in the unstretched network between the sensor points, or the length of a connecting element between two sensor points, is preferably between 1 cm and 4 cm, in particular between 1.5 cm and 3 cm. Due to the stretchability of the connecting elements, the distance between the sensor points when applied on the body can be significantly higher, with the sensor points having a distance in the range of 1 cm (unstretched "1 cm" connecting elements) to 12 cm (e.g. fully stretched 3-fold stretchable "4 cm" connecting elements).

The resulting network is preferably attached to a freely formed surface of a body, in the sense of an object. Preferably, both the sensor points and the connecting elements are connected to the body in a flat manner, in particular glued to it, or integrated into its layer structure. The sensor points measurably change at least one electrical property when external influences are applied to the body. Depending on the size and shape of the surface of the body to be covered, a different number of sensor points can be provided and linked as a network structure.

To achieve that the network can be glued on, it preferably comprises an adhesive layer. Preferably, the adhesive layer is present on one side of the sensor points and the connecting elements. In another embodiment, only the sensor points are provided with an adhesive layer. In another embodiment, only the connecting elements are provided with an adhesive layer.

In another embodiment, the sensor points and/or the connecting elements are provided with an adhesive layer on both sides.

In one embodiment, a peelable release film is present on the adhesive layer.

The body preferably has a surface curved in two dimensions. The body is preferably an object or a part of an object and not, as is also possible but less preferably, for example the body or a body part of a human being or animal. However, the body may be, for example, a tree, in particular a tree trunk.

The body preferably comprises plastic, foam, or wood, or is made entirely of one or more of these materials.

In one embodiment, the body, in the form of an object, has recesses for the sensor points. In one embodiment, the body, in the form of an object, has recesses for the connecting elements. In another embodiment, the body has recesses for the sensor points and the connecting elements. Preferably, the surfaces of the raised portions of the body surrounding the recesses lie flat with the sensor points and/or connecting elements inserted in the recesses. Preferably, several or all of the recesses for the sensor points have a distance from each other which is larger than the unstretched length of the connection elements of the sensor network. In other words, several or all of the connection elements are present in the stretched state on the body, in particular in the recesses on the body.

The body with sensor network is produced by first providing a body with recesses and then placing the sensor network in the recesses.

A corresponding use of the present sensor network is that the body is an object, wherein in a first step the object is created with recesses or provided with recesses, wherein after this first step on the object there are recesses in the size of the individual sensor points which recesses are spaced apart from one another, which recesses determine the positions of the sensor points, and wherein subsequently in the second step the network is placed on the body, wherein the sensor points of the network are thereby arranged in the recesses of the body.

Preferably, in the first step, the body is created or provided with additional recesses in the size of the connecting elements, which additional recesses for connecting elements connect the recesses for sensor points, and subsequently, in the second step, the network is placed on the body, with the sensor points of the network being arranged in the recesses for sensor points and the connecting elements being arranged in the additional recesses for connecting elements.

Preferably, a plurality of distances, which are each present between two sensor points and which are determined by the recesses, are longer than the unstretched length of the respective connecting element, which runs between the respective two sensor points. In other words, the arrangement of the recesses on the body deviates from the unstretched shape of the sensor network, whereby the sensor network can only be placed in the recesses on the body by stretching several connecting elements. Preferably, the body has a grid-like structure of recesses, wherein the grid-like structure is irregular, that is, with varying lengths of the edges of the grid-like structure. Preferably, the unstretched sensor network is present as a regular grid, that is, with identical lengths of all edges of the network. An edge of the network is defined as a connection between two nodes of the network.

In one embodiment, a protective layer is applied over the sensor network to fix the sensor network to the body and/or to provide desired surface properties.

Surface properties can be, for example: Material type, roughness, absorbency. The protective layer can be applied over a sensor network present in a raised position on the body. The protective layer can be applied over a sensor network present in recesses of the body. The protective layer may be applied as a fabric, film, or by curing of film-forming liquid. In one embodiment, the protective layer covers the connecting elements and the open spaces of the network, with the sensor points exposed or at least an area of the respective sensor point exposed.

In one embodiment, the carrier material of the sensor points can be a material that is stretchable in two dimensions. In another embodiment, the carrier material is not stretchable.

Preferably, the sensor network is embedded in a force-transmitting top layer (e.g. in soft varnish or in a bonded textile layer). The cover layer can be applied before or after attachment to the body. The cover layer can be facing the body or facing away from it.

Preferably, the sensor network is glued to the surface of the body.

In one embodiment, the sensor network can be detached from the body after use. The body is preferably deformable (intrinsically soft or thermoplastic).

The two-dimensional grid structure is preferably a rectangular, in particular square, grid.

Preferably, the meshes of the network are arranged according to passages in the body. This ensures that air or liquid can pass through the body and the sensor network.

Preferably, before the sensor network is attached, markings are made at defined points on the body to which the sensor points are attached when the sensor network is attached. In this way, the position of each sensor is predetermined.

In a preferred use of the sensor network, which is attached to the surface of a body, external impacts on the body are detected by measuring the electrical properties of each sensor point in the network and then linking the measured values to known positions of the sensors on the body. For this purpose, the shape of the body and the position of the markings on the body are preferably recorded in a virtual 3D model of the body, and the measured values of the sensor points are linked to the position data of the 3D model. For example, the pressure load at defined points on the body can be recorded in this way.

Preferably, the measured values of the sensor points are displayed according to a color scale (e.g. green-yellow-red scale) on the virtual 3D object of the body.

Preferably, a video is created from a large number of cyclically repeated measurements, representing the change over time of the measured values of the sensor points on the virtual 3D object.

Preferably, many such measurements are stored in a database and used for analysis (e.g. gait analysis when sensors are placed in a shoe or prosthesis).

In one embodiment, the measured values are displayed on the real body by projecting a representative representation, such as a color scale or a brightness value, onto the position of the respective sensor. In another embodiment, LEDs corresponding to the arrangement of the sensor points on the body may be present, which are driven representative of the measured values of the sensor points. The attachment of the LEDs can be done with an additional network or in another way.

Preferably, measurements are taken and stored from many sensor networks on different bodies and are used for further analysis (e.g., to evaluate properties of different types of bodies or the effects on a body in different environments).

SUMMARY OF THE INVENTION

The invention comprises a method for performing measurements on a body, wherein:

a digital model of the body is created in a first step, in a second step positions of measuring points are placed in the digital model, in a third step, a sensor network comprising sensor points and stretchable connecting elements between the sensor points is attached to the real body, the sensor points on the real body being arranged at the positions of the measuring points in the digital model, in a fourth step, at least one measurement of measuring values is performed at the sensor points.

The invention comprises a method for performing measurements on a body, wherein:

in a first step the body is created with markings for measuring points, or the body is provided with markings for measuring points, in a second step, a sensor network comprising sensor points and stretchable connecting elements between the sensor points is attached to the body, the sensor points being arranged on the body at the positions of the markings for the measuring points, in a third step, at least one measurement of measuring values is performed at the sensor points.

In the case of creating a body, the body is to be understood as an object. Providing a body with marking is possible with bodies in general.

The two methods can be advantageously combined by performing the first step of the second method (providing markings on the real body corresponding to the digital measurement points) before the third step of the first method.

In both methods, a two-dimensional sensor network is used to perform measurements on a body, which network comprises sensor points as nodes of the network and stretchable connecting elements between the sensor points as edges of the network, and which network has at least two edges in each of its two dimensions, which form grid lines of the network, wherein the network of sensor points and connecting elements is open in the region between the edges, and wherein the stretchable connecting elements comprise a stretchable substrate and a conductor. The sensor network is attached to the real body while individually stretching the individual connecting elements, wherein the sensor points on the real body are arranged at the positions of the measuring points in the digital model and/or at the positions of the markings on the body.

In preferred embodiments of these methods, the measured values at the sensor points are linked by software to the measuring points in the digital model. In particular, the actual measured values are displayed in real time at the positions of the measuring points in the digital model and/or the actual measured values are stored in a temporal course in the digital model for the measuring points. For this purpose, the measured value, the time stamp or time of the measurement and the position data of the measuring point in the digital model or on the body are stored in a database.

Preferably, the position data of the real body in space is also recorded and/or the motion sequence of the real body in space is recorded. This is done, for example, by video recordings, by position detectors in the room, or by additional motion sensors on the body. Preferably, with the inclusion of this data, the actual measured values at the positions of the measurement points are displayed in a digital motion model in real time and/or the actual measured values are stored in the digital motion model in the course of time to the measurement points. For this purpose, the measured value, the time stamp or time of the measurement, the position data of the measuring point in the digital model or on the body, and the current absolute and/or relative position of the respective measuring point in space are stored in a database.

The measured value at the respective sensor point depends on the parameter to be measured. The measured parameter therefore causes a change in at least one electrical property of a sensitive material or sensitive element of the sensor point.

The change in electrical properties of the electroactive layer or sensitive element when an external influence is applied to the body can be resistive, piezoresistive, piezoelectric or capacitive, or an impedance change.

The sensitive element can also be a thermocouple, a chemical sensor, or a photosensitive element such as a photoresistor or photodiode.

The interconnection of the sensor points in the network is preferably done as passive or active matrix interconnection.

The sensor signals of the network are preferably tapped via collecting elements, which are located on two adjacent and transverse sides of the network. Each collecting element runs along one dimension of the two-dimensional network. Preferably, the collecting element comprises at least one collecting conductor per line of sensor points present along this dimension which is aligned transverse to that dimension. Preferably, the collecting elements are implemented according to the connection elements, wherein a collecting element comprises an expandable substrate in which a plurality of electrical conductors made of non-expandable material are integrated in a winding path.

The collecting elements preferably lead to electronics which digitize the measurement signals. The electronics are preferably also attached to the body. The electronics may be connected to a data processing system, either by cable or by a wireless data transmission device.

The network structure is preferably regular, so that each element or mesh of the network, which is enclosed by four connecting elements, has the same shape and size in the unstretched state.

Preferably, all connecting elements of the network, which each connect two sensor points and are arranged parallel to each other, have the same unstretched length.

Preferably, all connecting elements of the network, which each connect two sensor points, have the same unstretched length.

The stretchable connecting elements each comprise a stretchable substrate and at least one, preferably exactly one, conductor of non-stretchable material, wherein the conductor does not extend in a straight path along the substrate such that the length of the conductor is longer than the length of the connecting element. The conductor is preferably non-redundant so that it provides exactly one conductive path along the connecting element.

Preferably, the length of the conductor on a piece of substrate is 1.25 times to 4 times longer than the unstretched length of the piece of substrate, especially 1.5 times to 3 times, more preferably at least 2 times.

In one embodiment, a connecting element is fabricated by integrating at least one elongated non-stretchable metal body into a stretched stretchable layer, the metal body folding or meandering after relaxation of the layer.

In one embodiment, a connecting element is fabricated by integrating at least one folded or meandered non-stretchable metal body into an unstretched stretchable layer.

By both embodiments a connecting element is obtained, which is stretchable and conductive. The conductivity of the connecting element does not change during stretching, because the length and the cross-section of the metal body remain unchanged (Only the angle between the folded or meandering sections of the metal body changes).

In one embodiment, the conductor is in the form of a spiral.

In one embodiment, the conductor is meander-shaped.

In one embodiment, the conductor is present with a zigzag course.

In one embodiment, the conductor is present with a sinusoidal shape.

Preferably, the conductor is enclosed in the substrate, wherein connection points are present at both ends of the stretchable connecting element. Preferably, the conductor is located between two film layers of the substrate.

The substrate is preferably a plastic film. The plastic is preferably an elastomer.

The connecting elements are preferably in the form of flat elements, with the surfaces of the connecting elements lying in the plane of the surfaces of the sensor points. The connecting elements are preferably rectangular, with the longer side of the rectangle forming an edge of the network and the conductor running in the longitudinal direction of the rectangle.

The sensor points or the sensors may be of a wide variety of types, and the sensors may have preferred features described herein. Sensors that are different from one another can also be attached to a sensor network.

Each sensor point has at least one sensitive element, wherein at least one electrical property (for example, the ohmic resistance) of the sensitive element is dependent on a measured quantity.

The sensitive element is located between two contacts of the sensor point, one of these contacts being connected to connecting elements of a first grid line of the network and the second of these contacts being connected to connecting elements of a second grid line of the network, the two grid lines being transverse to each other and crossing in the sensor point.

In one embodiment, a diode is present at at least one sensor point, which is connected in series with the sensitive element of the sensor point. This allows the sensor point to be controlled directionally selectively. A diode arranged in the same direction at each sensor point prevents current flow in undesired directions in the network, so that so-called crosstalk between the sensor points is prevented.

In one embodiment, a transistor is present at at least one sensor point, which is connected in series with the sensitive element of the sensor point, whereby an additional control line is present at the control input of the transistor. For the control line of the transistor, an additional conductor is present at a connection element which connects to the sensor point, or an additional connection element is present for the control line. As a result, the sensor point can be individually controlled via the control line of the transistor by switching the transistor to be conductive or non-conductive.

In one embodiment, the sensor point has a planar or two-dimensional structure, whereby the current flow or a capacitive coupling takes place in one plane. This means that the elements of the sensor point in the form of conductor tracks, sensitive element and optionally diode or transistor are present in the plane of the carrier material or in a plane on the carrier material of the sensor point and the current flow or a capacitive coupling also takes place in this plane. An example of such a structure is a sensor in the form of a finger electrode with interlocking comb-like electrodes which are present in one plane.

In one embodiment, the sensor point has a sandwich configuration in which the sensitive element or material is between two electrodes, with the planar extent of the electrodes parallel to the plane of the network and current flow or capacitive coupling between the electrodes, through the sensitive material, perpendicular to the plane of the network. The electrodes, which represent conductor tracks, thus lie in parallel planes that are spaced from one another in a direction perpendicular to the surface of the sensor point. This embodiment with current flow in several planes parallel to the surface of the sensor point and current flow or capacitive coupling perpendicular between these planes is herein referred to as a three-dimensional structure of the sensor point.

In this embodiment, a first conductor line or connection point is present at the first electrode and a second connection point is present at the second electrode. The connecting elements of a first grid line of the network are connected to the first electrode and the connecting elements of a second grid line of the network are connected to the second electrode, whereby the two grid lines are transverse to each other and cross at the sensor point. The connecting elements are connected to the two opposite flat sides of the sensor point.

For the sensor points, it is preferred that these have four connection points to which connection elements can be attached in an electrically conductive manner. Preferably, a first pair of these connection points lies on a line that is aligned parallel to the first dimension of the network. Preferably, the second pair of these connection points lies on a line that is aligned parallel to the second dimension of the net.

Preferably, the respective pair of connection points is connected by an electrical conductor or an uninterrupted conductor path at the sensor point.

Preferably, all connection points that lie along a grid line of the network are electrically conductively connected by connecting elements.

In one embodiment, the sensor point comprises a non-conductive carrier material on which at least one conductor track is present.

The conductor track is formed from conductive material applied to the carrier material.

The sensor preferably comprises a non-conductive carrier material that can be penetrated by an ambient medium. The carrier material is preferably present as a thin sheet-like layer, for example in the form of a sheet or a strip.

A penetrable carrier material is understood to be a carrier material having openings extending from one side of the carrier material to the other.

The penetrable carrier material may be a film, fabric, nonwoven fabric, fiber mat, or open-cell foam or sponge. The material may first be manufactured as a dense layer and then processed into a penetrable carrier material by perforations. For example, a film can be processed into a penetrable carrier material by perforation.

In particular, the penetrable carrier material can be formed from paper, fabric, glass fibers, mineral fibers, or non-conductive plastic.

Preferably, the penetrable carrier material continues to be penetrable in the area of the conductor track, which means that the conductive material does not close the openings of the penetrable carrier material.

The conductive material is present on at least one side of the carrier material.

Preferably, the conductive material in the area of the conductor tracks completely envelops the material of the carrier material. This means that the material of the conductive tracks is present on both sides of the carrier material, with the material of the conductive tracks on the two sides being in contact with each other through the openings of the carrier material.

In other words, the material of the conductor track preferably completely envelops the material of the carrier material, which is present between two adjacent openings of the carrier material. Preferably, openings of the carrier material remain open in the area of the conductor track and are not closed by the material of the conductor track.

The sensors of the network can be used to measure temperature, density changes, mechanical deformations (pressure, strain, compression, bending), chemical state changes (e.g. curing of adhesives), wetness, liquid penetration, pH, biological growth processes, concentration of biomolecules, destruction, cracking.

Contacting the conductor tracks on the carrier material can be carried out by soldering electrical leads directly to the conductor track. A terminal can be placed on both sides of the carrier material on a conductor track. A conductive material can be glued to the conductor track.

The carrier material and/or the conductive tracks can be provided with reactive surfaces in order to be able to measure pH or light, for example.

By using two separate electrodes in an interleaved or interlocking comb structure of their conductor tracks, changes in the electrical properties of the surrounding medium, or of the carrier material in the space between the comb structure, can be detected with high sensitivity.

Temperature change and/or strain can be measured using single conductors or single conductor tracks with contact points at both ends.

Thermocouples can be constructed with two intersecting conductive paths made of different metals—e.g. nickel-chromium/nickel (type K). This takes advantage of the fact that two conductors made of different metals have a thermoelectric effect at the contact surface.

Preferably, the carrier material is a maximum of 2000 μm thick, particularly preferably a maximum of 500 μm, especially a maximum of 50 μm.

Preferably, the carrier material has a porosity of at least 10%, more preferably at least 50%, in particular at least 75%.

Preferably, the carrier material has an average pore size of at least 1 μm, more preferably at least 10 μm, in particular at least 100 μm.

Preferably, the sensor point in the area of the conductive track or conductive material has an average porosity of at least half the porosity of the carrier material.

Preferably, the sensor point in the area of the conductive track or conductive material has an average pore size of at least half the pore size of the carrier material.

The material of the conductive tracks is preferably a conductive metal, in particular aluminum, copper, silver or gold, with copper being particularly preferred. In addition, carbon black and conductive polymers can be used.

Preferably, the material of the conductive tracks is present in a layer thickness of at most 30% of the average pore size, particularly preferably at most 10%, especially at most 1%.

In one embodiment, the porosity can be selected so that the sensor appears largely transparent and can thus blend in well with a visually appealing environment.

The average transmittance of the sensor point is preferably at least 10%, especially at least 20%, particularly preferably at least 50%, especially at least 75%.

The high transmission is preferably achieved by porosity, which means that the material (e.g. the fibers) of the carrier material is not transparent and/or the material of the conductive tracks is not transparent.

In one embodiment, the porosity of the carrier material already provided with conductive material or of the sensor point already provided with conductive tracks can be increased by perforating it. The perforation can be done mechanically or by laser or by electro perforation. This perforation can be carried out in the area of the conductor tracks and/or in the area between the conductor tracks.

DETAILED DESCRIPTION

The embodiments shown in the figures merely illustrate possible embodiments, whereby it should be noted at this point that the invention is not limited to these specifically illustrated embodiments thereof, but combinations of the individual embodiments with each other and a combination of an embodiment with the above general description are also possible. These further possible combinations need not be explicitly mentioned, since these further possible combinations are within the skill of the person skilled in the art working in this technical field, based on the teaching for technical action by the present invention.

Figure 1:
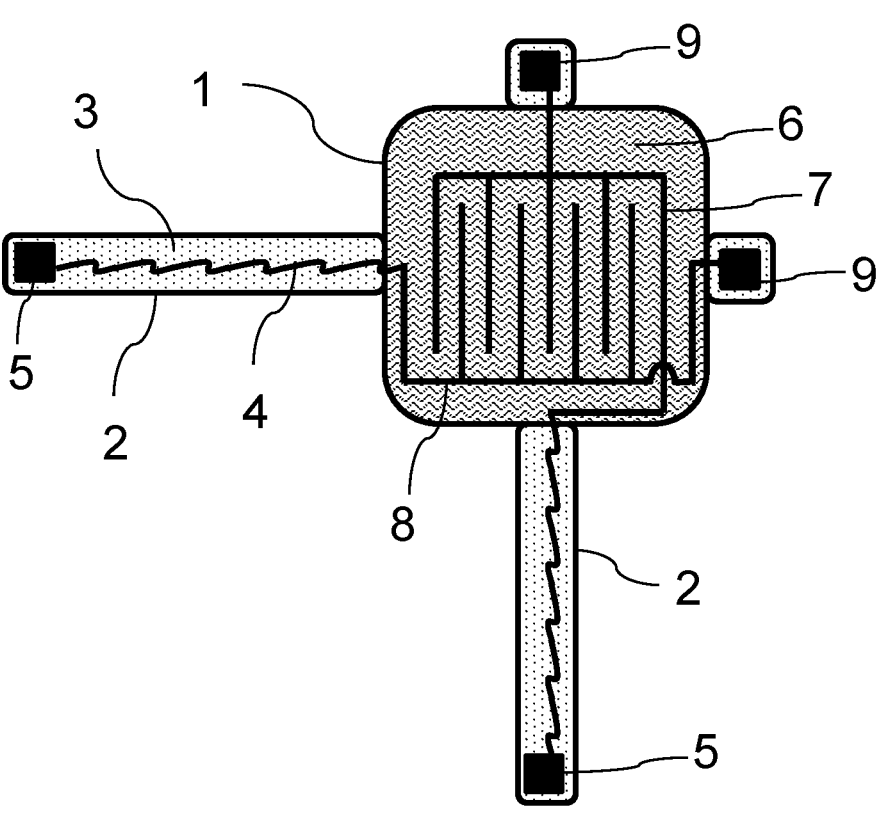
FIG. 1: Schematically illustrates an embodiment of a sensor point with two connecting elements.

FIG. 1 illustrates the basic structure of the sensor points 1 and connecting elements 2 by means of an example.

The connecting elements 2 comprise a stretchable substrate 3. A conductor 4 of non-stretchable metal is present on or in the stretchable substrate 3. The conductor 4 runs in a sinuous or bent course, so that the individual sections of the conductor 4 run transversely or not parallel to the longitudinal direction of the connecting elements 2. When the length of the substrate 3 changes, the angle of the individual sections of the conductor 4 to the longitudinal direction changes, but not the cross-section and the length of the conductor 4. As a result, the electrical resistance of the conductor 4 remains constant when the length of the substrate 3 changes.

The conductor 4 can be contacted at both ends of the connecting element 2. For this purpose, the conductor 4 itself can be exposed on the substrate 3 or project beyond the substrate 3 in the longitudinal direction. Between the contact points at the two ends of the connection element 2, the conductor 4 is preferably insulated in that the conductor 4 itself has insulation or, in particular, is preferably embedded in the substrate 3. For example, the conductor 4 may be present between two layers of the substrate 3 in the form of films.

The conductor 4 is preferably a single strand, but may also comprise several strands. The material of the conductor 4 is preferably copper. The conductor 4 is preferably twisted into a spiral and flattened. The spiral is flattened or formed into a two-dimensional shape. Alternatively, the conductor 4 may be formed into a zigzag or meander or sinusoidal two-dimensional shape by bending or folding.

The two-dimensional structure of the formed conductor 4 can then be stretched and applied to a stretched substrate 3 in the stretched state. Alternatively, the two-dimensional structure can be applied to an unstretched substrate 3 in an unstretched or compressed state.

One or both of the contact points on the connection element 2 can be present as a connection point 5, which is in the form of a two-dimensional surface on the substrate 3 whose two dimensions each exceed the thickness of the conductor 4. This facilitates contacting, in particular soldering.

The sensor points 1 have a carrier material 6, on which carrier material 6 at least one conductor track 7 runs.

In the case of only one conductor track 7, the conductor track 7 itself is the sensitive element of the sensor point 1, one end of the conductor track being in contact with a connecting element 2 extending in a first direction away from the sensor point 1 and the second end of the conductor track being in contact with a connecting element 2 extending in a second direction away from the sensor point 1, the first and second directions being transverse to one another, in particular at an angle of 90 degrees.

Preferably, however, at least two conductor tracks 7, 8 run along the sensor point 1 which are not in direct contact. A sensitive material or a sensitive element is present between the conductor tracks 7, 8, which enables a current flow from the first conductor track 7 to the second conductor track 8 or a capacitive coupling between the conductor tracks 7 and 8 depending on an externally acting input variable.

The first conductor track 7 is either contacted with one connection element 2, which runs in a first direction. Or the first conductor track 7 is contacted with two connection elements 2, which run in the first direction. The second conductor track 8 is either contacted with a connection element 2, which runs in a second direction. Or the second conductor track 8 is contacted with two connection elements 2 which run in the second direction. The first and the second direction are transverse to each other, in particular at an angle of 90 degrees.

The sensor point 1 preferably has at least one connection point 9 for each of the two directions, which is present in the form of a two-dimensional surface on the carrier material 6 whose two dimensions each exceed the width of the conductor track 7. In one embodiment, two connection points 9 are present for each of the two directions.

Preferably, each connection point 9 is located centrally on the respective side edge of the carrier material 6.

The connection point 9 may be located on the carrier material 6 or may be present as an additional element adjacent to the carrier material 6, as shown.

In the embodiment of FIG. 1, the sensitive element of the sensor point 1 is the carrier material 6 itself, which is present between the conductor tracks 7 and 8. The comb structure of the interleaved conductor tracks 7, 8 increases the sensitivity. The connection points 5 and 9 lying horizontally on a line are directly connected by the conductor track 8 and the conductor 4 of the connection element 2, so that the same electrical potential is present at these connection points. The connection points 5 and 9 lying vertically on a line are directly connected by the conductor track 7 and the conductor 4 of the connection element 2, so that the same electrical potential is present at these connection points.

When a voltage is applied to one of the two conductor tracks 7, 8, a current flow results through the carrier material 6 towards the other conductor track 7, 8, so that the voltage at the second of the two conductor tracks 7, 8 is a measure of the quantity (such as moisture) acting on the carrier material 6.

Figure 2:
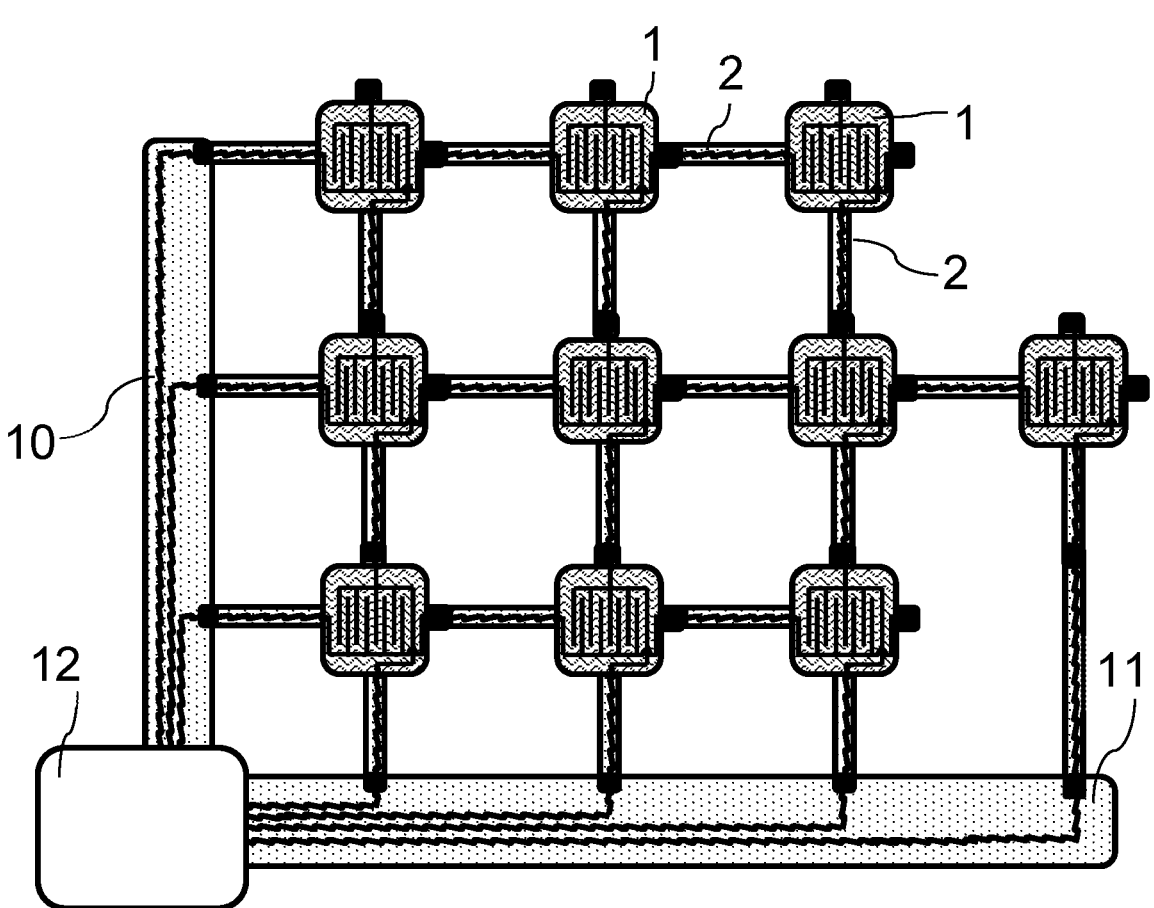
FIG. 2: Schematically illustrates the connection of several sensor points by connecting elements to form a network.

FIG. 2 illustrates how several sensor points 1 and connecting elements 2 can be arranged to form a network and how a measuring circuit for the network can be implemented.

The sensor points 1 form the nodes of the network, which are connected by the connecting elements 2 (edges of the network) in a straight path. Four connecting elements 2 form a mesh, and the network is open in space inside the meshes.

The network has grid lines that run in two directions that are transverse to each other.

All sensor points 1, which are present on a grid line, are connected along the grid line by connecting elements 2. The grid lines are connected to an electronic evaluation unit 12 via collecting elements 10, 11, whereby one collecting conductor per grid line runs on one of the collecting elements 10, 11 from the respective grid line to the electronic evaluation unit 12 (in the case of a passive matrix).

Preferably, the collecting conductors of the collecting elements 10, 11 are designed according to the conductors 4 of the connecting elements 2. Preferably, the substrate of the collecting elements 10, 11 is designed according to the substrate 3 of the connecting elements 2.

During the measuring process, an electrical energy or a voltage or a signal is always applied to one of the collecting conductors after the other of a first collecting element 10 in order to always switch only one grid line of a first direction of the network active. The other grid lines of the same direction are preferably connected to ground (GND). The collecting conductors of the second collecting element 11 transmit the measuring signals of the sensor points 1 which are located at the intersections of the grid lines of the second collecting element 11 and the active grid line of the first direction.

Figure 3:
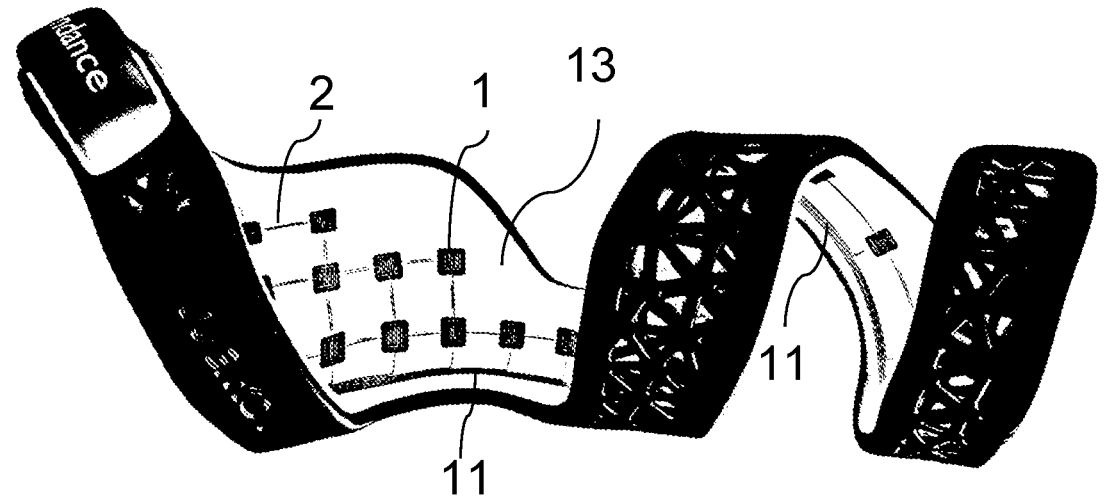
FIG. 3: Illustrates an exemplary use of a sensor network on a body.

FIG. 3 illustrates the attachment of a sensor network to a body 13. The position of the sensor points 1 on the body 13 are predetermined and preferably marked on the body 13.

By stretching the connecting elements 2, the network can be adapted to different distances between parallel grid lines (especially rows and columns).

In addition, the body itself can stretch and deform during the measurement without the measurement result being affected by changes in the length of the conductors 4 or the network being destroyed by breakage of the conductors 4.

The body 13 of FIG. 3 is, for example, a garment or support element made of plastic and/or fabric that is attachable to a body part of a person or animal.

Figure 4:
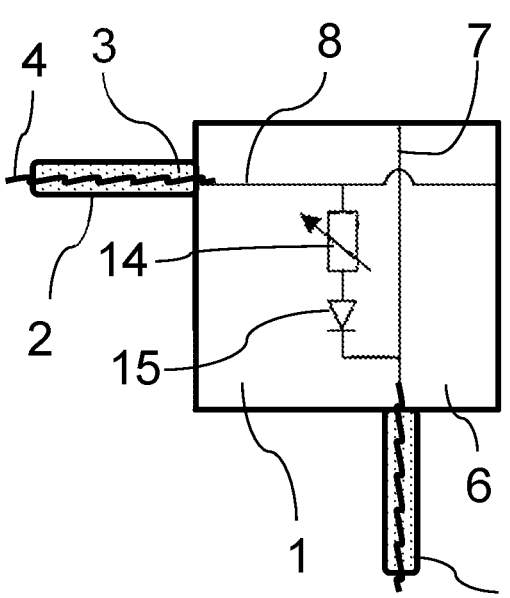
FIG. 4: Shows an embodiment of a sensor point with a diode.

FIG. 4 illustrates a sensor point 1 which comprises a sensitive element 14, for example in the form of an ohmic resistance variable by a measured variable, and comprises a diode 15 in series with it. A current flow is possible from conductor track 8 to conductor track 7 via the sensitive element 14 and the diode 15 in the forward direction. Current flow from conductor track 7 to conductor track 8, on the other hand, is blocked by diode 15. In one embodiment, each sensor point 1 of the network comprises a diode 15 which prevents current flow from the grid lines of a first direction to the grid lines of a second direction.

Figure 5:
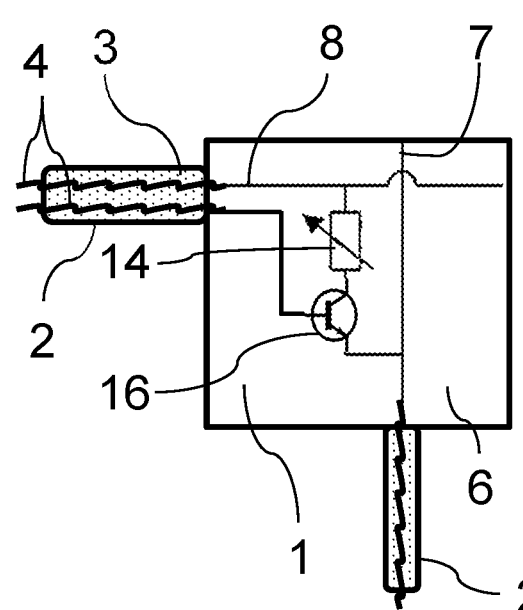
FIG. 5: Shows an embodiment of a sensor point with a transistor.

FIG. 5 illustrates a sensor point 1 which comprises a sensitive element 14, for example in the form of an ohmic resistance variable by a measured variable, and a transistor 16 in series with it. A current flow is possible, for example, when an npn transistor is used, from the conductor track 8 to the conductor track 7 via the transistor 16 if a voltage is present at its base or switching input. Generally formulated, in this embodiment any type of transistor 16 is attached to the sensor point 1 in order to make the current path between the transverse connection elements 2 at the sensor point switchable. When the sensor points 1 of FIG. 5 are arranged to form a network, each transistor 16 can be provided with its own control line to make each individual sensor point individually switchable.

Figure 6:
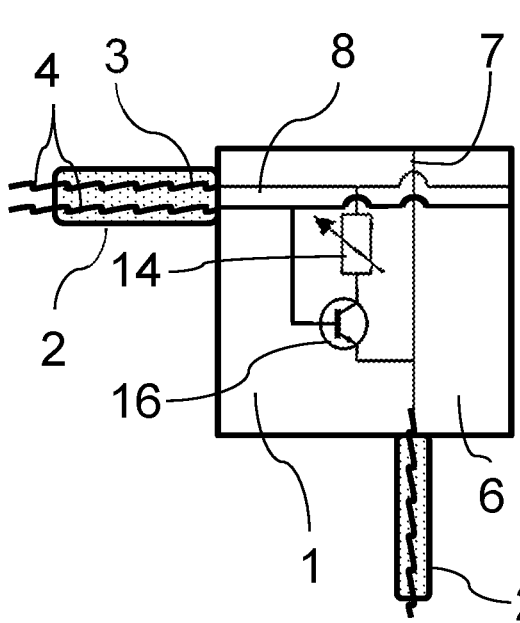
FIG. 6: Shows a second embodiment of a sensor point with a transistor.

In the embodiment of FIG. 6, connection points for the control line are present at sensor point 1 on two opposite edges of sensor point 1 in order to be able to connect the control lines of the sensor points along a grid line.

Figure 7:
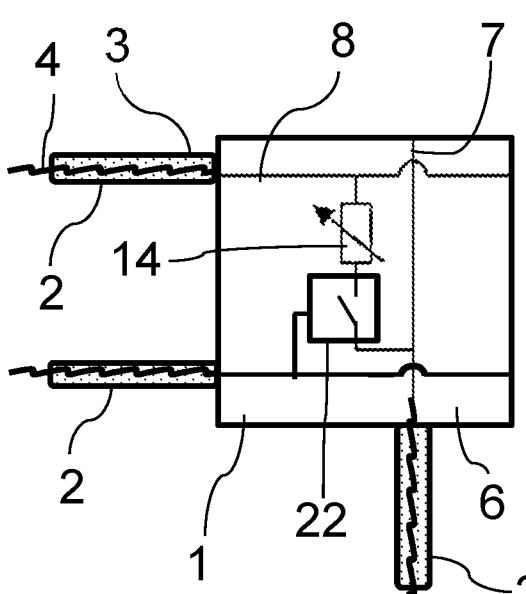
FIG. 7: Shows an embodiment of a sensor point with an addressable switch.

In FIG. 7, an addressable switch 22 is connected to the sensor point. The control line in this case is a digital data line. This allows each individual sensor point 1 to be switched individually, even if they are on a common control line.

As illustrated in FIGS. 5 and 6, a conductor 4 for the control line and a conductor 4 for one of the conductor tracks 7, 8 may be present on a common connecting element 2.

As illustrated in FIG. 7, a separate connection element 2 with a single conductor 4 can be connected to the sensor point 1 for the control line.

Figure 8:
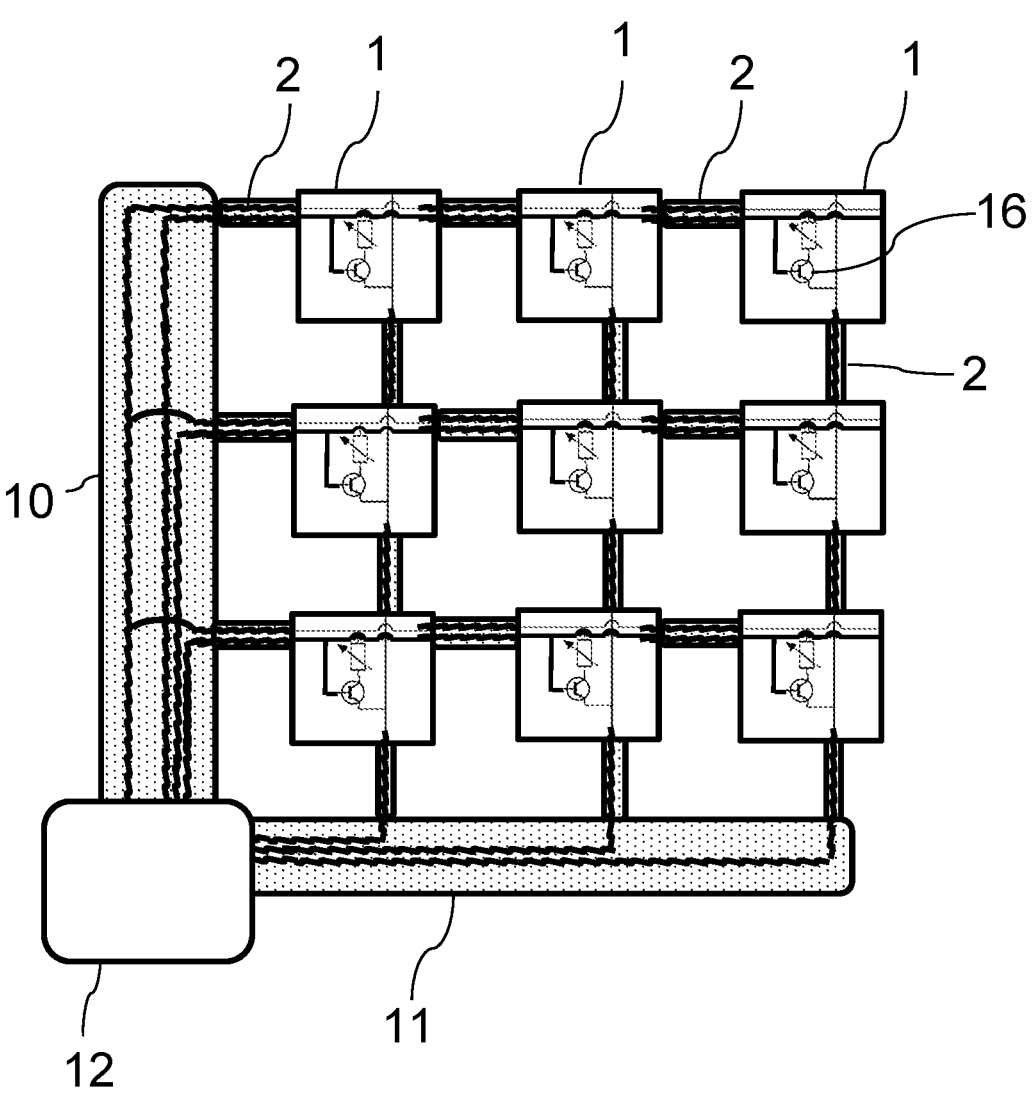
FIG. 8: Shows a network with active matrix circuit.

FIG. 8 illustrates a network of sensor points 1 with transistors 16. The control lines of the sensor points are interconnected along the grid lines of the first direction of the network. The conductor tracks 7, 8 of the sensor points 1, which are connected in this first direction, can all be at a common potential, or at a common conductor, since the switching of the individual grid lines during the measuring process by the transistors 16 via their common control lines is carried out by switching one control line after the other actively during the measuring process.

Figure 9:
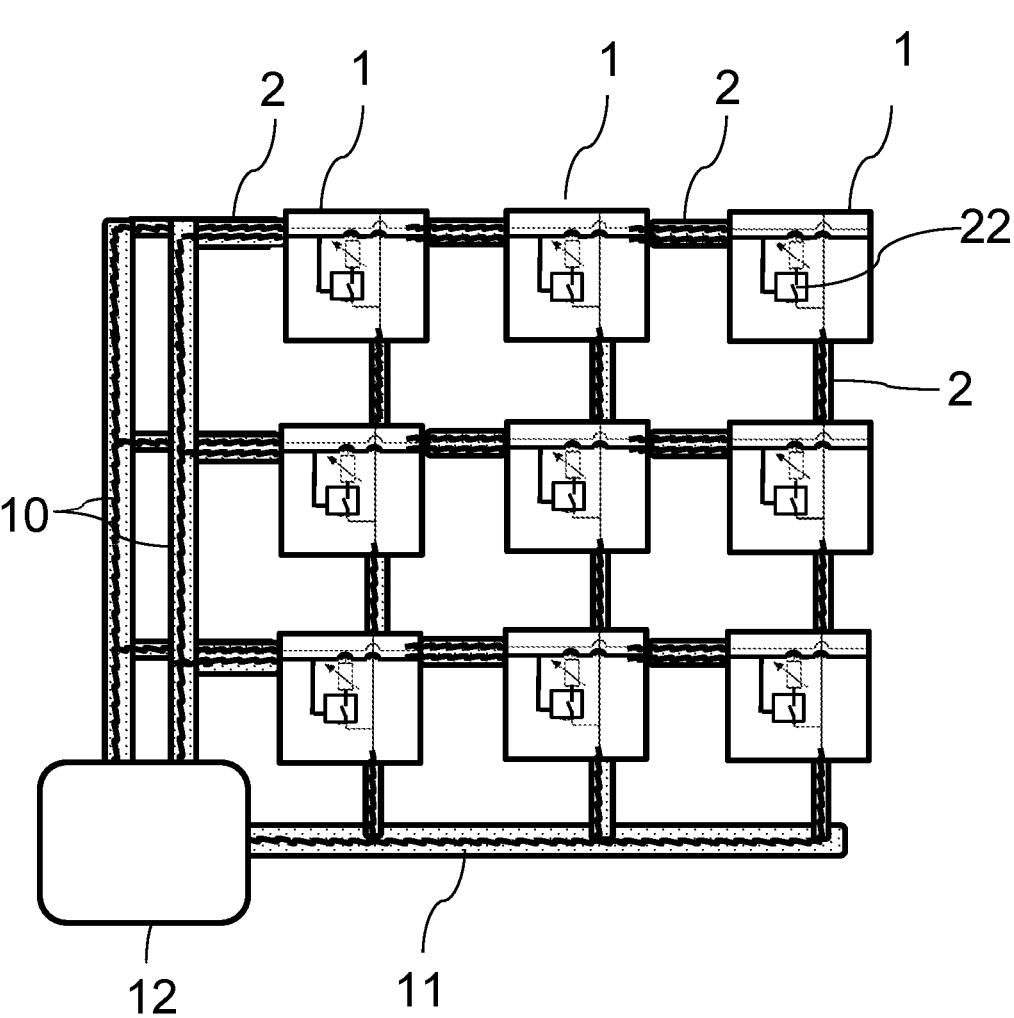
FIG. 9: Shows a network with addressable sensor points.

FIG. 9 illustrates a network of sensor points 1 with addressable switches 22. The control lines of all sensor points 1 are interconnected, wherein this can be done by connecting elements 2 along the grid lines of the first direction of the network, wherein these can all be connected to a common collecting conductor. The sensor points are thus present as a bus with bus topology.

The traces of the sensor points, which are connected in a common direction of the network, can all be at a common potential, or at a common collecting conductor, since the switching of individual sensor points during the measurement process can be done by their address via the bus.

Figure 10:
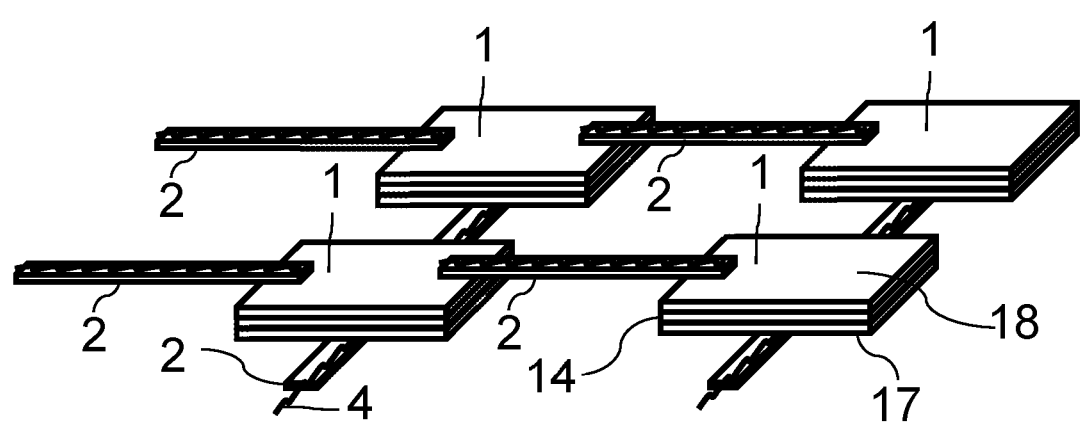
FIG. 10: Shows sensor points with electrodes in a sandwich configuration.

In FIG. 10, sensor points 1 with sandwich structure are schematically illustrated. The sensor points 1 have a first electrode 17, which corresponds to the first conductor track 7 of the previous embodiments, and a second electrode 18, which corresponds to the second conductor track 8 of the previous embodiments. The electrodes 17, 18 each have a two-dimensional planar structure which extends in the plane or parallel to the plane of the network. The electrodes 17, 18 can extend over the entire surface of the sensor point 1 or only over a partial surface. Between the electrodes 17, 18, the sensitive element 14 or a sensitive material is present, which changes at least one electrical property as a function of a measured variable.

The interconnection in the network is effected in that the first electrodes 17 are each connected along a grid line of a first direction by connecting elements 2 and the second electrodes 18 are each connected along a grid line of a second direction by connecting elements 2, the two directions being transverse, in particular at right angles, to one another. Advantageously, the conductor tracks 7, 8 or the electrodes 17, 18 are in different planes. Otherwise, if crossing points of the conductor tracks 7, 8 of the sensor are in one plane, as in FIG. 1 in the lower, right-hand corner region of the sensor point 1, then an insulating intermediate layer must be present between the conductor tracks 7, 8 at this point. The sensor point 1 of FIG. 10 has a "three-dimensional" structure.

Figure 11:
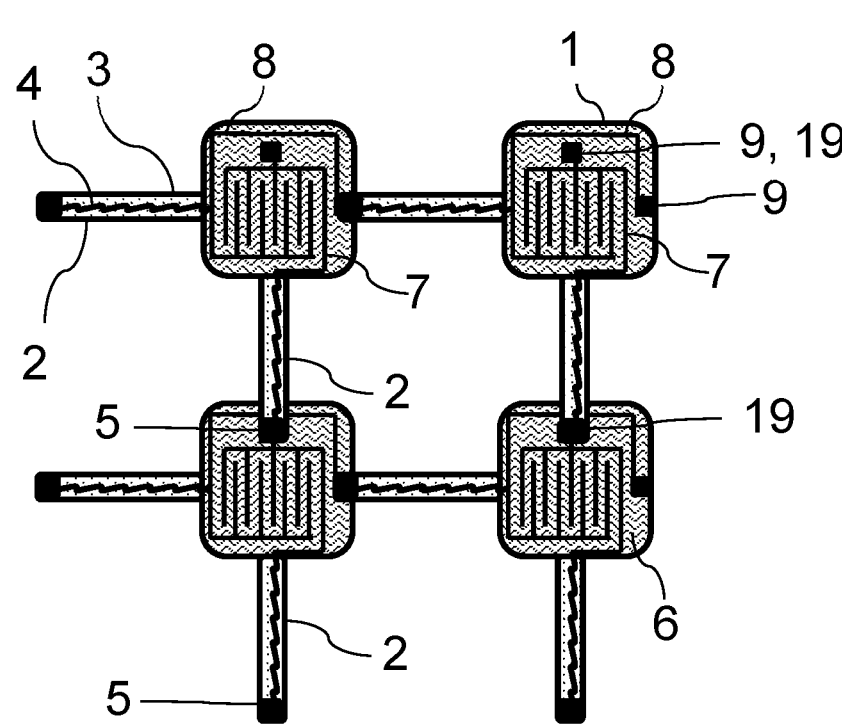
FIG. 11: Shows an embodiment with finger electrodes.

FIG. 11 illustrates a modified form of the embodiment in FIG. 1, in which crossings of the conductor tracks 7, 8 at the "two-dimensional" sensor point 1 are avoided. This is achieved by routing one conductor track 8 externally around the connection point 9 of the other conductor track 7. The conductor track 7 thus has an inner connection point 19. When a connection element 2 is attached to the inner connection point 19, the conductor 4 of the connection element 2 crosses the conductor track 8, with the electrically insulating substrate 3 of the connection element 2 being present between conductor 4 and conductor track 8.

Figure 12:
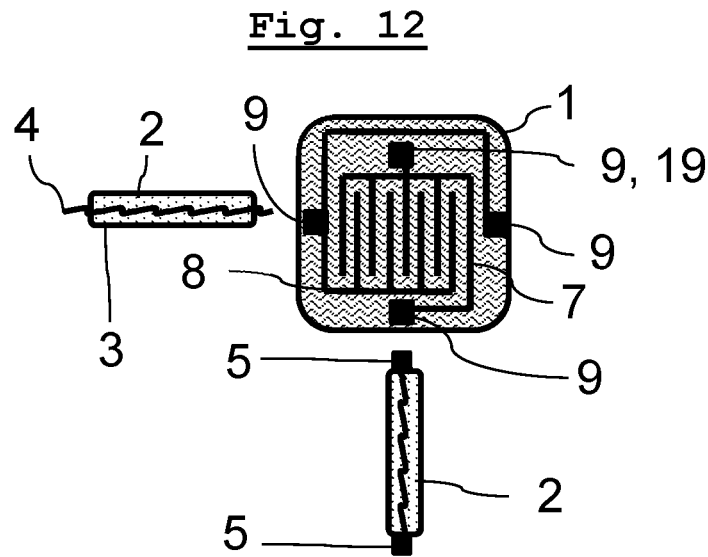
FIG. 12: Shows an embodiment of sensor points and connection elements.

FIG. 12 shows a kind of kit system for sensor networks, comprising sensor points 1, which have four connection points 9, and connecting elements 2, which have connection options, in particular connection points 5 at both ends. The four connection points 9 are preferably each arranged centrally along one of the four side edges of the sensor point 1. The connection possibilities or connection points 5 of the connection elements 2 can be formed in that the conductor 4 of the connection element 2 is exposed, or alternatively a connection point 5 is conductively connected to the conductor 4 (both variants are illustrated). By attaching the free conductor ends or connection points 5 of the connecting elements 2 to the connection points 9 of sensor points 1, any number of sensor points 1 and connecting elements 2 can be arranged along rows and columns (first and second directions of grid lines that are transverse to each other) to form a network.

Figure 13:
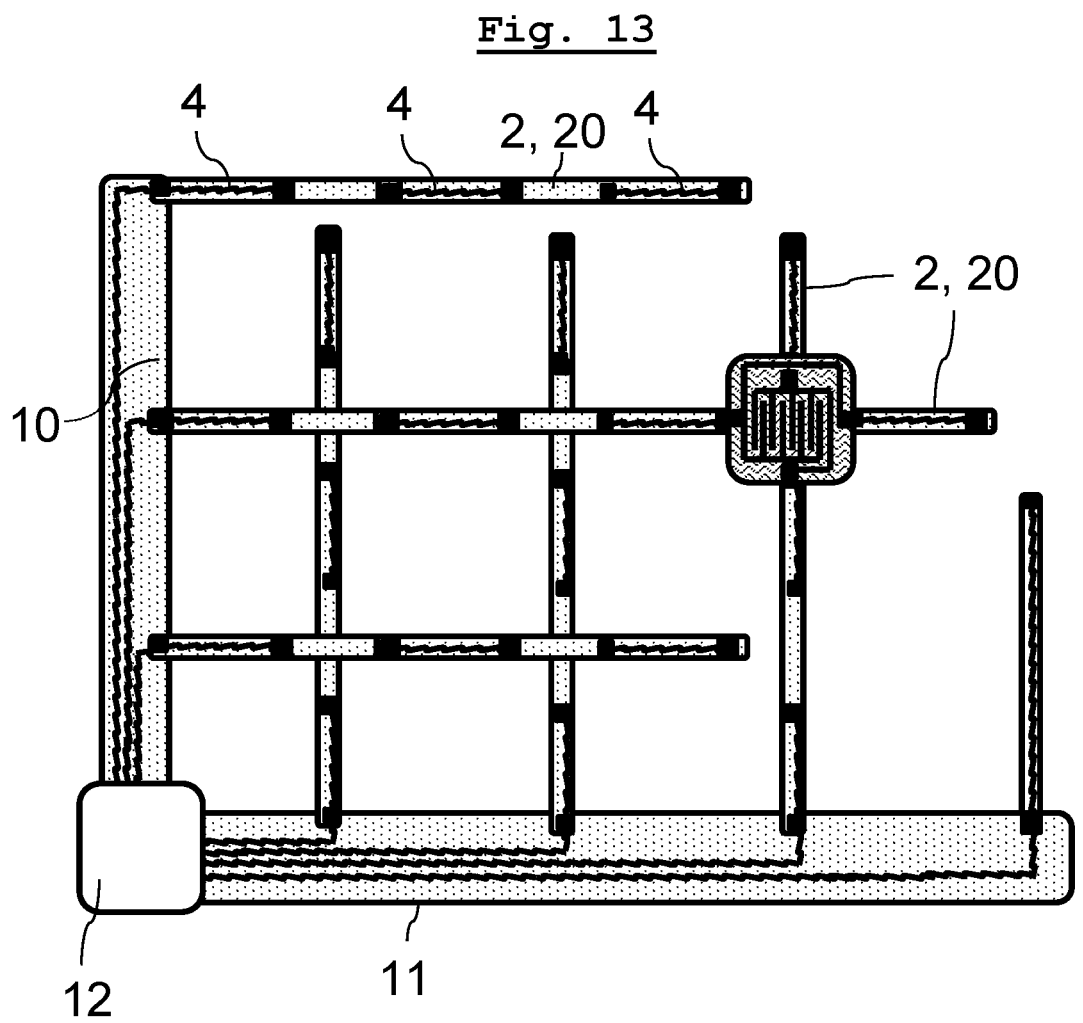
FIG. 13: Shows a first embodiment of connecting elements in the form of connecting lines.

In FIG. 13, a further embodiment of connection elements 2 is shown, which extend in the form of connection lines 20 along entire grid lines of the network. In the example of FIG. 13, a plurality of conductors 4 are arranged on a substrate 3 of each connecting line 20, wherein the longitudinal direction of the conductors 4 is arranged in the longitudinal direction of the substrate 3 and there are spaces between the conductors 4 in the longitudinal direction. Connection facilities or connection points 5 are provided at both end portions of each conductor 4. As is illustrated, sensor points 1 may be arranged at crossing points, T-points and corner points of each of a connecting line 20 of a first direction and each of a connecting line 20 of a second direction, transverse to the first. The intersection points of the connecting lines 20 behind the sensor points 1 are thereby formed by the substrate 3. The substrate 3 of the connecting lines 20, which is present between two connection points 9 of a sensor point 1, can optionally be removed after the network has been formed.

Figure 14:
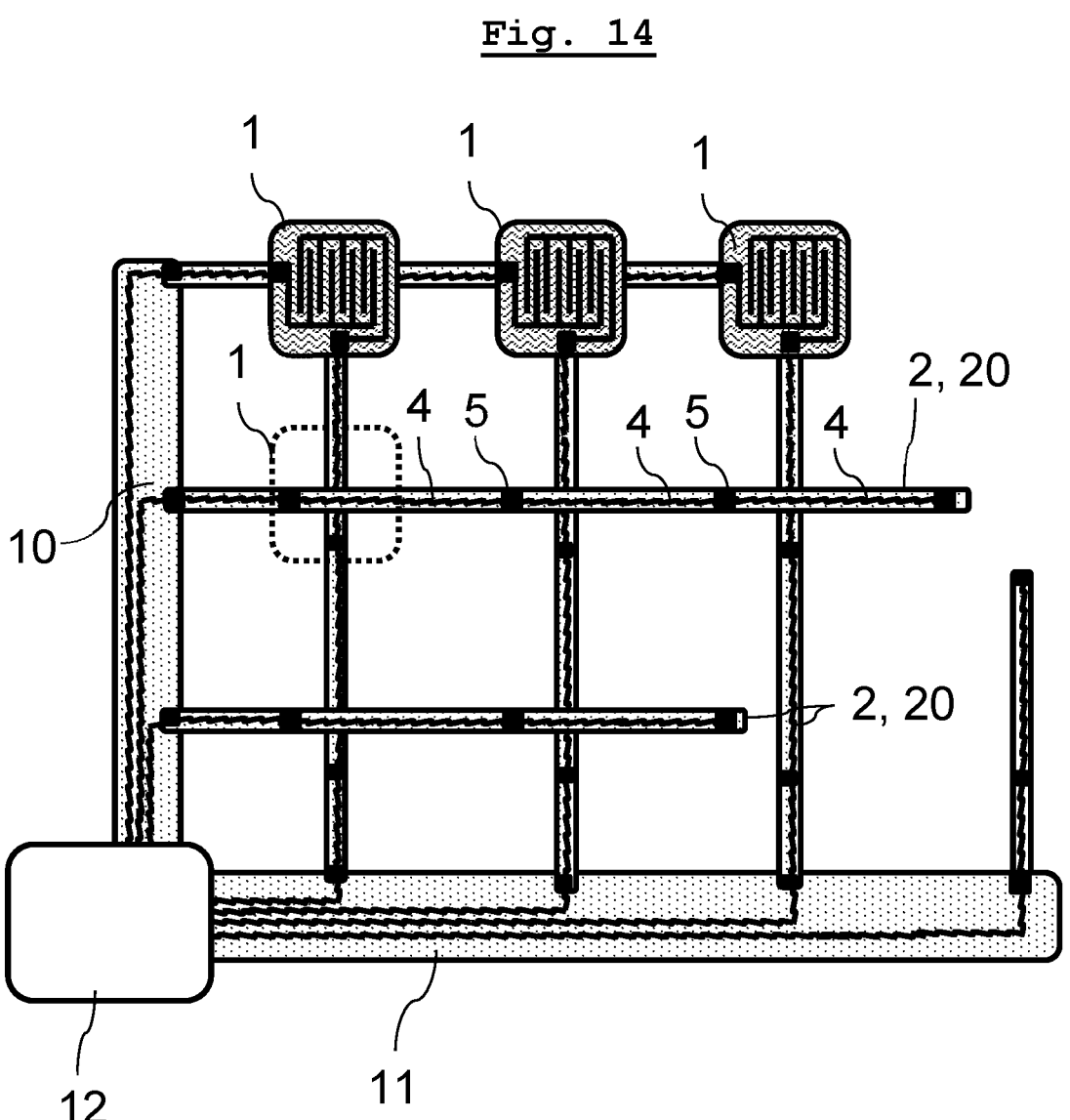
FIG. 14: Shows a second embodiment of connecting lines.

FIG. 14 shows another embodiment of connection elements 2, which extend in the form of connecting lines 20 along entire grid lines of the network. In contrast to FIG. 9, these have a continuous conductor 4, so that the current flow along the respective grid line happens through the conductor 4. Along the connecting line 20, connection possibilities are provided at a distance from one another, at which the conductor 4 or a connection point 5 conductively connected to the conductor 4 is exposed for contacting. In this case it is sufficient if the sensor point 1 has only one connection possibility or one connection point 9 per grid direction. The connection of the sensor points 1 of each grid line is achieved by the conductor 4, which runs behind or in front of the surface of the sensor point 1 and is electrically insulated from the sensor point 1 by the substrate 3.

Connecting elements 2 in the form of connecting lines 20 are also particularly suitable for three-dimensional sensor points or sensor points with a sandwich structure, for example as shown in FIG. 10, where the connecting lines 20 of the two grid directions are present in different planes and thus run across the sensor point 1 on opposite surfaces thereof.

Figures 15A, 15B, 15C, 15D:
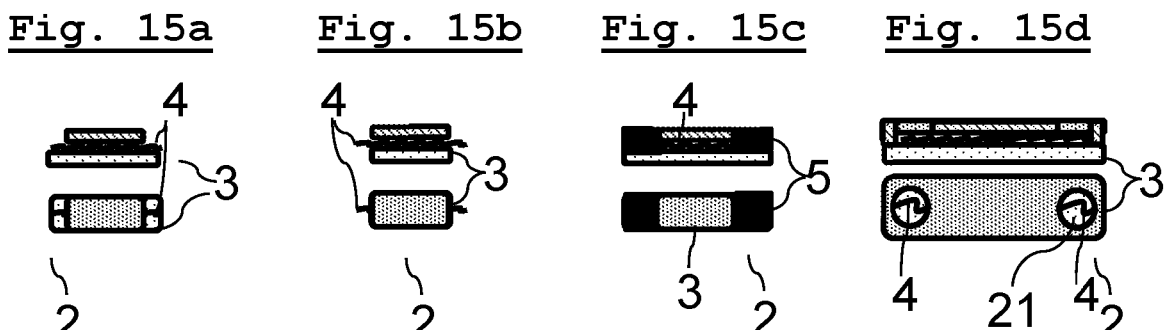
FIG. 15: Illustrates exemplary embodiments of connecting elements.

In FIGS. 15a to 15d, possible embodiments of connecting elements 2 for connecting two sensor points 1 to each other are shown in a view from the front and from above. As shown, the conductor 4 may be present between two layers of the substrate 3, the two layers preferably consisting of the same material, in particular elastomer. As shown in FIG. 15a, the first layer can be longer than the second layer, with the conductor 4 exposed on both sides of the second layer on the first layer.

As shown in FIG. 15b, the first layer and the second layer may be of equal length, with the conductor 4 protruding on both sides between the layers.

As shown in FIG. 15c, in a modification of FIG. 15a, conductive material can be present at the free end of conductor 4 as a connection element or connection point 5.

As shown in FIG. 15d, the conductor 4 may be enclosed on all sides between two layers of a substrate 3, with an opening 21 at each end region of the connecting element 2 in the planar region of at least one of the layers.

Figure 16:
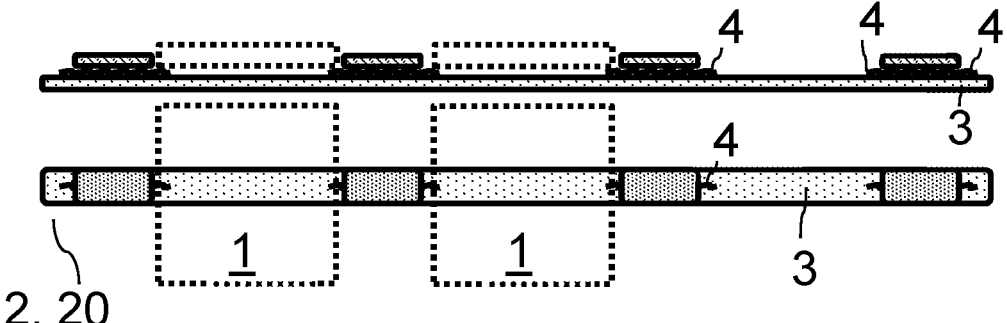
FIG. 16: Illustrates an embodiment of a connecting line.

FIG. 16 shows a possible embodiment of a connecting line 20 (embodiment of FIG. 13), wherein a strip of an insulating material is applied over a partial area of each individual conductor 4, both ends of each individual conductor 4 being exposed on both sides of the strip. The strips are preferably in the form of an elastomeric film in the same way as the continuous substrate 3 of the connecting line 20.

Figure 17:
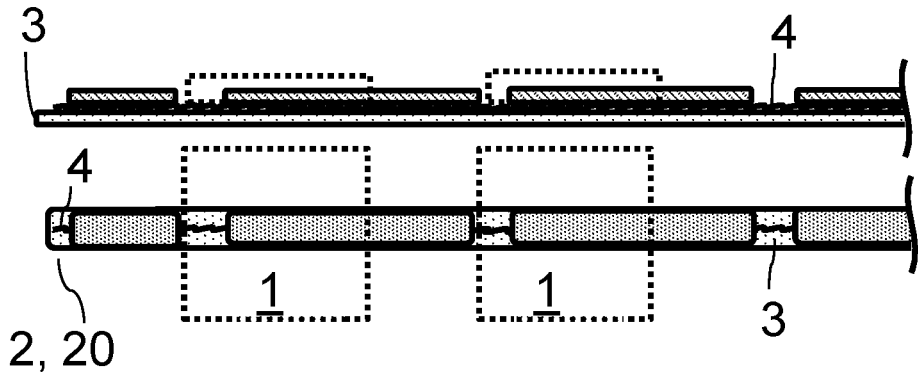
FIG. 17: Illustrates a further embodiment of a connecting line.

FIG. 17 shows a possible embodiment of a connecting line 20 (embodiment of FIG. 14), wherein a strip of an insulating material is attached to each of several partial areas of the single conductor 4, wherein the strips are spaced apart from one another in the longitudinal direction of the substrate 3 and the single conductor 4 is exposed between the strips. The strips are preferably present as an elastomeric film in the same way as the continuous substrate 3 of the connecting line 20.

Figure 18:
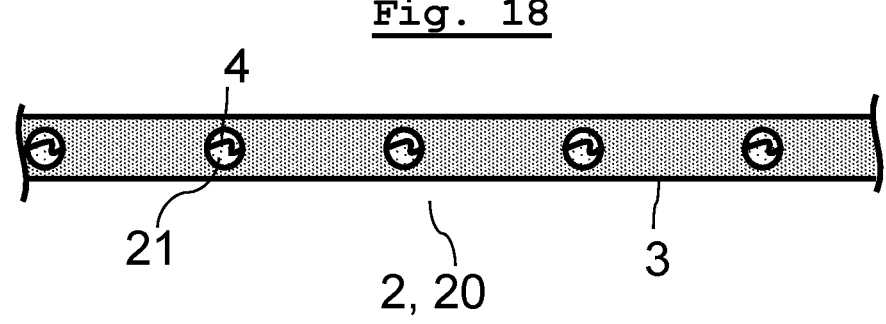
FIG. 18: Illustrates a further embodiment of a connecting line.

FIG. 18 shows a possible embodiment of a connecting line 20 (embodiment of FIG. 14), wherein the single conductor 4 is present between two layers of the substrate 3, or between two elastomeric films. At least one of the layers is provided with a plurality of openings 21 spaced apart from one another in the longitudinal direction of the connecting line 20, the single conductor 4 being exposed in the region of the openings 21.

Connection elements or connection points 5 may be present at or instead of the free ends or sections of the conductors 4 of FIGS. 16-18. For example, the openings 21 can be closed or cast with conductive material.

For machine production of the connectors 2, a continuous web or an unwound strip of the substrate 3 can be transported through a machine which positions a two-dimensionally deformed conductor 4 either continuously or singly in sections on the substrate 3, and wherein a second layer of a substrate is positioned either continuously or in strips over the conductor 4. The two-dimensional deformation of the conductor 4 may thereby be performed in the machine, or the conductor 4 may be fed to the machine in the two-dimensionally deformed state.

Optionally, the machine can attach connection points 5 in the area of the connections of the continuous web.

The two layers of substrate material can be joined by gluing, welding or pressing.

At the output of the machine, an endless or long belt of connecting lines is obtained, in particular according to one of FIGS. 16 to 18, from which endless belt connecting lines 20 of the required length or individual connecting elements 2 according to FIGS. 15a, 15c and 15d can be cut off.

The embodiments of FIGS. 15a and 15b can also be achieved by positioning an "endless" conductor 4 between two "endless" layers of substrate 3, wherein after cutting off the individual connecting elements 2, at least one (FIG. 15a) or both (FIG. 15b) of the layers of substrate 3 is/are removed at both end regions of the connecting element 2.

The substrate 3 or the bands or strips of the substrate 3 are present in a width which is wider than the width of the area occupied by the two-dimensional shape of the conductor.

In another manufacturing embodiment, the two-dimensionally deformed conductor 4 can be enclosed in the substrate 3 by placing it on one half of a wider strip or web of substrate 3, the other half of which is folded around the conductor 4, the free ends of the two halves being joined together, in particular welded or glued.

It is also possible to place several two-dimensionally deformed conductors 4 parallel to and at a distance from each other on a wide film web or a wide film strip and to cover them with a second wide film web or a second wide film strip, the film webs or film strips being bonded or welded in the areas between the conductors 4. By cutting the film webs or film strips in the longitudinal direction, individual connecting lines 20 can be obtained, and by cutting them in the transverse direction, individual connecting elements 2 can be obtained.

Of course, connecting lines 20 and connecting elements 2 can also be obtained in this way, which contain two or more parallel and mutually spaced conductors 4 (e.g. for collecting elements 10, 11 or for connecting elements 2 or connecting lines 20, which have a "measuring conductor" and a "control conductor" or "bus conductor").

The invention claimed is:

1. A two-dimensional network comprising:
sensor points forming nodes of the network; and
elongated connecting elements comprising a substrate and a conductor forming edges of the network;
wherein the network has in each of its two dimensions at least two edges of the edges forming grid lines of the network, the network of sensor points and connecting elements being open in an area between the edges;
wherein at each sensor point a current flow or a capacitive coupling couples the conductors of a first grid line to the conductors of a second grid line, the first and second grid lines being transverse to one another and the current flow or the capacitive coupling being dependent on a measured parameter of the sensor point; and
wherein the connecting elements each have a stretchable substrate, which substrate is present as a straight strip, on which at least one conductor is present, which runs from a first end region of the connecting element along a longitudinal direction to a second end region of the connecting element, the conductor including a non-stretchable material and the conductor having a wound course or a bent course on the stretchable substrate, so that individual sections of the conductor run transversely with respect to the longitudinal direction of the respective connecting element.

2. The two-dimensional network according to claim 1, wherein the substrate is an elastic plastic film.

3. The two-dimensional network according to claim 1, wherein the conductor includes metal.

4. The two-dimensional network according to claim 1, wherein all conductors present along a common grid line of the network are one of directly conductively connected and connected by conductor tracks present at the sensor points.

5. The two-dimensional network according to claim 1, wherein at least at some sensor points there is a component in a form of a diode, a transistor, or an addressable switch, which component is arranged in a current path of the sensor point between the conductors of the first grid line and the conductors of the second grid line.

6. The two-dimensional network according to claim 1, wherein a first conductor track and a second conductor track are present at least at one sensor point, the first conductor track being electrically connected to the conductors of the first grid line and the second conductor track being directly connected in an electrically conductive manner to the conductors of the second grid line, the first grid line crossing the second grid line in a region of the sensor point, and a material or element which is sensitive to the measured parameter being present between the first conductor track and the second conductor track.

7. The two-dimensional network according to claim 1, wherein the connecting elements are stretchable by at least 1.25 times.

8. The two-dimensional network according to claim 1, wherein a length of the conductor is at least 1.5 times the straight length of the substrate along which it runs with a winding course or a zigzagging course.

9. The two-dimensional network according to claim 1, wherein the conductors of each of the respective grid lines of the network are connected to a common collection conductor or to a respective collection conductor of a collection line, which collection lines lead to an electronic evaluation unit.

10. A use of the two-dimensional network according to claim 1, wherein the two-dimensional network is attached to a body.

11. The use according to claim 10, wherein:
the body has markings at positions for attaching sensor points; and
at least some of the sensor points are attached to the markings while stretching their connecting elements.

12. The use according to claim 10, wherein adjacent markings are spaced at least the distance of the unstretched connecting elements from each other and wherein at least some adjacent markings have a distance from each other which is greater than the length of the unstretched connecting elements.

13. The use according to claim 10, wherein the network is attached to a surface of the body that is curved in two dimensions.

14. The use according to claim 10, wherein the body is an object, the object or at least one surface or inner layer of the object having openings corresponding to the meshes of the network.

15. The use according to claim 10, wherein the body is an object in the form of a support device for a body part of a living being or an object in the form of a garment.

16. The use according to claim 10, wherein the body is deformable or elastic in the region of the network.

17. The use according to claim 10, wherein:
a digital model of the body is created, the digital model comprising at least a surface of the body and a position of the sensor points of the sensor network on the body; and
measured values of the individual sensor points of the sensor network are linked by software to their position in the digital model.

18. The use according to claim 10, wherein:
the body is an object, where in a first step the object is created or provided with recesses;
thereafter on the object there are recesses in a size of the individual sensor points and spaced apart from one another, which recesses define the positions of the sensor points; and
subsequently in a second step the network is placed on the body, the sensor points of the network being arranged in the recesses of the body.

19. The use according to claim 18, wherein:
in the first step, the body is created or provided with additional recesses in a size of the connecting elements, which additional recesses for connecting elements connect the recesses for sensor points; and subsequently in the second step, when the network is placed on the body and the sensor points of the network are placed in the recesses, the connecting elements being placed in the additional recesses for connecting elements.

20. The use according to claim 18, wherein a plurality of distances which are present between respective two sensor points and which are predetermined by the recesses are longer than the unstretched length of the respective connecting element which runs between the respective two sensor points.

21. A method for performing measurements on a body with a two-dimensional sensor network comprising sensor points as nodes of the network and stretchable connection elements between the sensor points as edges of the network and which network has in each of its two dimensions at least two edges which form grid lines of the network, wherein the network of sensor points and connecting elements is open in the area between the edges and wherein the stretchable connecting elements comprise a stretchable substrate and a conductor, comprising:

creating, in a first step, a digital model of the body;

placing, in a second step, positions of measuring points in the digital model;

attaching, in a third step, the sensor network to the real body while individually stretching the individual connection elements, whereby the sensor points are arranged on the real body at the positions of the measuring points in the digital model; and performing, in a fourth step, at least one measurement of measuring values at the sensor points.

22. A method for performing measurements on a body with a two-dimensional sensor network comprising sensor points as nodes of the network and stretchable connection elements between the sensor points as edges of the network and which network has in each of its two dimensions at least two edges forming grid lines of the network, wherein the network of sensor points and connecting elements is open in the area between the edges and wherein the stretchable connecting elements comprise a stretchable substrate and a conductor, wherein:

manufacturing or providing, in a first step, the body with markings for measuring points;

attaching, in a second step, the sensor network to the body, with stretching of the individual connecting elements, the sensor points being arranged on the body at the positions of the markings for the measuring points; and performing, in a third step, at least one measurement of measuring values at the sensor points.

\* \* \* \* \*